United States Patent [19]

Aghili

[11] Patent Number: 4,687,499

[45] Date of Patent: Aug. 18, 1987

[54] PROCESS FOR SEPARATING HYDROCARBON GAS CONSTITUENTS

[75] Inventor: Hafez K. Aghili, Katy, Tex.

[73] Assignee: McDermott International Inc., New Orleans, La.

[21] Appl. No.: 847,071

[22] Filed: Apr. 1, 1986

[51] Int. Cl.⁴ .................................................. F25J 3/02
[52] U.S. Cl. .......................................... 62/24; 62/32; 62/42
[58] Field of Search ...................... 62/23, 24, 31, 32, 42

[56] References Cited

U.S. PATENT DOCUMENTS

| | | | |
|---|---|---|---|
| 3,398,543 | 8/1968 | Horton | 62/11 |
| 3,849,096 | 11/1974 | Kniel | 62/23 |
| 4,162,273 | 7/1979 | Skraba | 62/24 |
| 4,171,964 | 10/1979 | Campbell et al. | 62/24 |
| 4,235,613 | 11/1980 | Castoe et al. | 62/24 |
| 4,278,457 | 7/1981 | Campbell et al. | 62/24 |
| 4,368,061 | 1/1983 | Mestrallet et al. | 62/24 |
| 4,370,156 | 1/1983 | Goddin, Jr. et al. | 62/24 |
| 4,410,342 | 10/1983 | Horton | 62/23 |
| 4,453,958 | 1/1984 | Gulsby et al. | 62/28 |
| 4,464,190 | 8/1984 | Gulsby et al. | 62/24 |

Primary Examiner—Ronald C. Capossela
Attorney, Agent, or Firm—Robert J. Edwards; Michael L. Hoelter

[57] ABSTRACT

A process for separating natural gas constituents wherein a portion of the residue gas from the demethanizer column is cooled, expanded, partially condensed and recycled to the top of this column. This alters the chemical equilibrium in the column causing the lighter methane to vaporize and separate from the heavier constituents such as ethane, propane, etc. The lighter methane constituent rises and is removed from the top of the demethanizer column while the heavier constituents fall and are removed from the bottom of this column.

14 Claims, 3 Drawing Figures

PROCESS FOR SEPARATING HYDROCARBON GAS CONSTITUENTS

FIELD OF THE INVENTION

This invention pertains to a method of separating hydrocarbon gas constituents such as ethane from methane in the natural gas and more particularly to a method by which such separation is essentially 100% complete.

BACKGROUND OF THE INVENTION

The history of separating gas constituents from natural gas is a relatively recent one. In the 1940's the first prototype natural gas cyrogenic turboexpander was built and in the 50's this turboexpander concept was applied to air plants, hydrogen plants, and helium purification plants. However, it wasn't until the 1960's that the first commercial natural gas turboexpander plant started operation. As commercial demand for these separated gases increased, many other such plants came into existence each with better and improved designs for separating the lighter elements (methane, ethane, and propane) from the heavier elements (butane, pentane and their iso-components) contained in natural gas.

Many patents exist pertaining to these improvements with some of the more relevant patents being those to Gulsby (U.S. Pat. Nos. 4,464,190 and 4,453,958), Horton (U.S. Pat. Nos. 4,410,342 and 3,398,543), and Campbell, et al. (U.S. Pat. Nos. 4,278,457 and 4,171,964). While each of these patents are improvements over their predecessors, none of them address the commercial need for the nearly 100% gas separation and recovery.

It is an object of this invention to provide a method for achieving 100% separation of the natural gas feed stream constituents. It is another object of this invention to utilize a true distillation column for the separation of these constituents. A further object of this invention is to provide a method of nearly 100% gas constituent separation in existing plants without requiring major plant restructuring.

SUMMARY OF THE INVENTION

This invention pertains to a method for separating light weight methane from the heavier constituents found in a natural gas stream. It includes a demethanizing tower having one or more feed lines, one or more reboiler lines (or heat exchange lines) and a true reflux system. The preferred embodiment of this process employs a high pressure separator and gas expander for the incoming feed line. A residue gas line coming from the top of the feed demethanizer column is used to chill the incoming natural gas afterwhich this residue gas is compressed and air cooled. A portion of this residue gas is subsequently chilled and then expanded in a reflux expander or by a flash control valve and returned to the top of the demethanizer column. This return line enables the demethanizer to operate as a true distillation column thereby achieving nearly 100% separation of ethane and heavier constituents from the lighter methane.

DETAILED DESCRIPTION OF THE DRAWINGS

Figure 1:
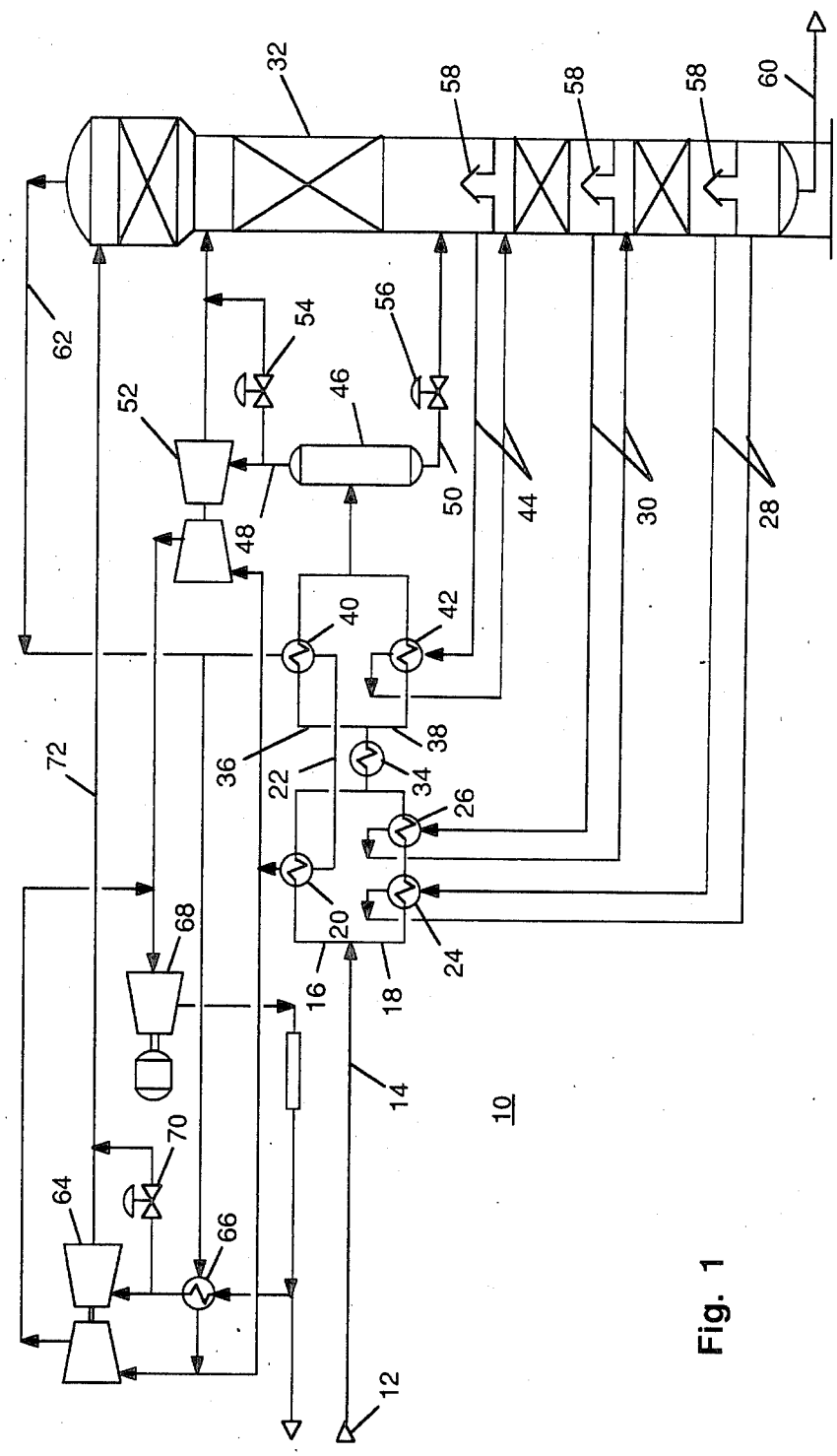
FIG. 1 is a schematic illustration of the various components of this invention and how they correlate including the demethanizer having a return reflux line.

Referring to FIG. 1, natural gas enters gas separator process 10 through inlet 12 after having first been dehydrated. This gas in line 14 is then divided into separate gas streams 16 and 18 respectively. Gas stream 16 is cooled in warm gas/gas exchanger 20 by residue gas in line 22. Gas stream 18 is cooled in reboiler 24 and lower side heater 26 through which demethanizer liquid flows via lines 28 and 30 from demethanizer column 32.

From these exchangers, cooled gas streams 26 and 18 recombine and enter gas chiller 34 where this combined stream is further cooled by a refrigerant. After chiller 34, this chilled stream is again separated into two portions, stream 36 and stream 38 for more cooling. Stream 36 is cooled in cold gas/gas exchanger 40 by cold residue gas directly from the top of demethanizer column 32. This residue gas is generally at a temperature of $-150°$ F. As shown, this cold residue gas passes first through cold gas/gas exchanger 40 before traveling through warm gas/gas exchanger 20 via line 22. Stream 38 is cooled in upper side heater 42 by demethanizer liquid flowing through lines 44 from demethanizer column 32. This demethanized liquid is generally at a temperature of $-130°$ F.

Cold gas streams 36 and then 38 then recombine and enter high pressure separator 46 where this cold inlet gas is separated into gas stream 48 and liquid stream 50. Gas stream 48, which by this time consists predominantly of the lighter methanes, ethanes, and propanes, is expanded to reduce its pressure such as by main expander 52 or across expansion valve 54. This expansion further cools the gas before it is fed into an upper region of demethanizer column 32. The condensed liquid stream 50 from high pressure separator 46 is also expanded, thereby reducing its pressure, such as across expansion valve 56, before entering the side of demethanizer column 32. By this time, liquid stream 50 consists predominantly of the heavier butanes, pentanes, and their iso-components.

As liquid is fed to demethanizer column 32, it flows downward under the force of gravity. During its journey, this liquid is engaged by rising vapors which strip the methane from this liquid as it passes through demethanizer column 32. This stripping operation produces a demethanized end product which is removed from the bottom of the demethanizer column 32 via line 60. These rising methane vapors are generated from the heat obtained from heat exchangers 24, 26 and 42 via lines 28, 30 and 44. The demethanizer column is equipped with packing or trays 58 to effect the distillation process.

Residue line 62 exits the top of demethanizer column 32 where its temperature is approximately $-150°$ F. A portion of this residue line, which is predominantly methane, is routed to cold gas/gas exchanger 40 and warm gas/gas exchanger 20 to cool the incoming gas streams 36 and 16. From these heat exchangers, the warmed residue gas is compressed by the compression side of main expander 52, as shown, or by reflux expander 64. The remainder of the residue from residue line 62 passes through reflux heat exchanger 66, where it is warmed before being compressed by the compression side of reflux expander 64. After initial compression, this vapor is further compressed by turbine recompressor 68 after which it is cooled and transported elsewhere.

A portion of the residue gas is cooled or condensed by reflux heat exchanger 66 and then either expanded into liquid form across reflux expander 64 or across flash valve 70. This predominantly liquified reflux is then returned to the top of demethanizer column 32 via reflux stream 72 where its addition radically alters the chemical equilibrium in column 32 causing the heavier elements to remain in a liquid state falling to the bottom while causing more of the lighter methane to vaporize and rise in column 32. It is this recycling of the reflux to column 32 that results in column 32 acting as a distillation column thereby achieving a higher degree of gas separation and recovery of the heavier elements from the natural gas feed.

Figure 2:
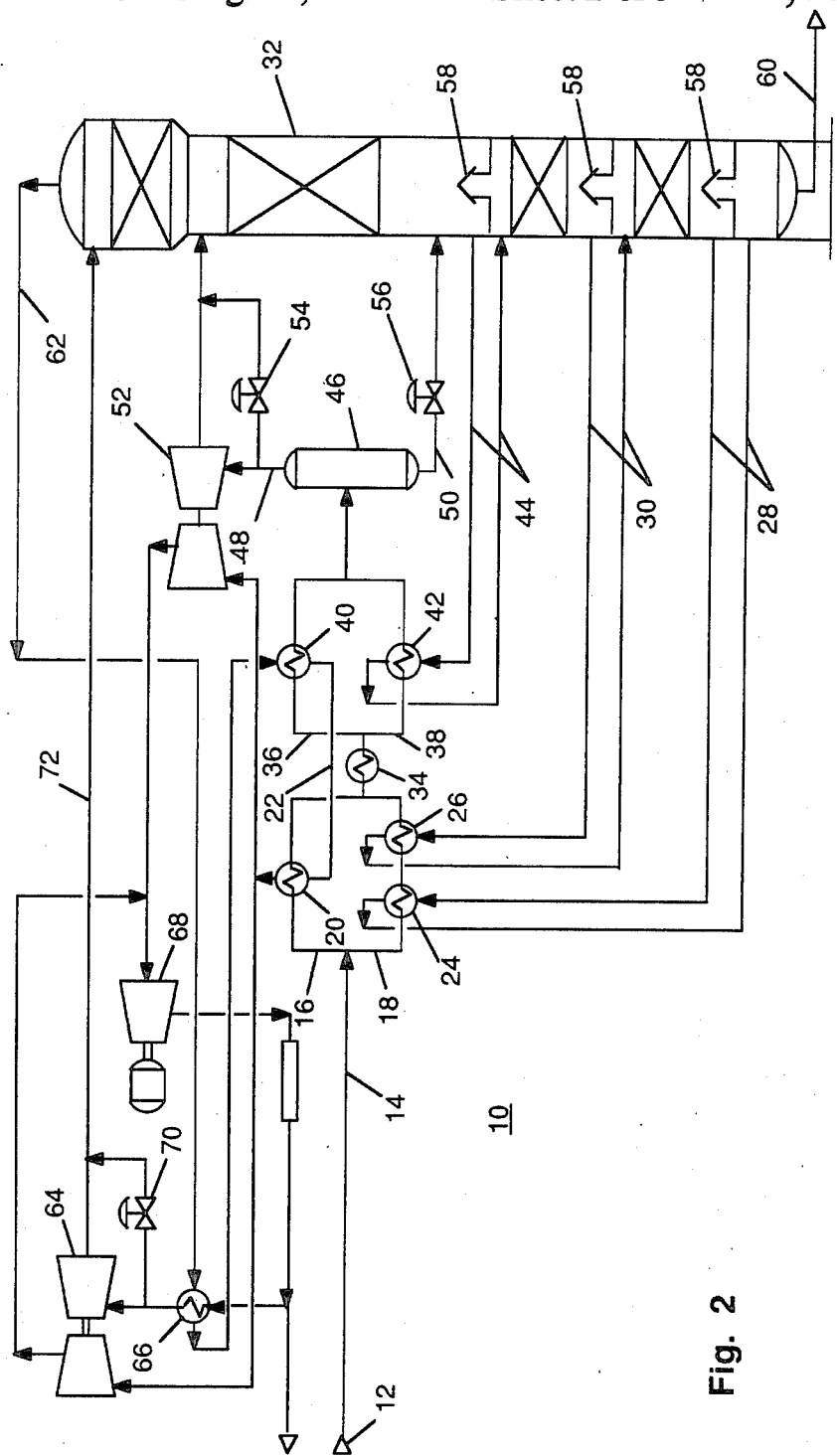
FIG. 2 is an alternate schematic illustration wherein the residue gas from the demethanizer flows first through a reflux exchanger before passing through a heat exchanger.

Another arrangement for the heat exchange of the reflux system is shown in FIG. 2. In this case, the total residue stream coming from demethanizer 32, via residue line 62, flows through reflux exchanger 66 first and then through cold gas/gas exchanger 40 and warm gas/gas exchanger 20 respectively.

Figure 3:
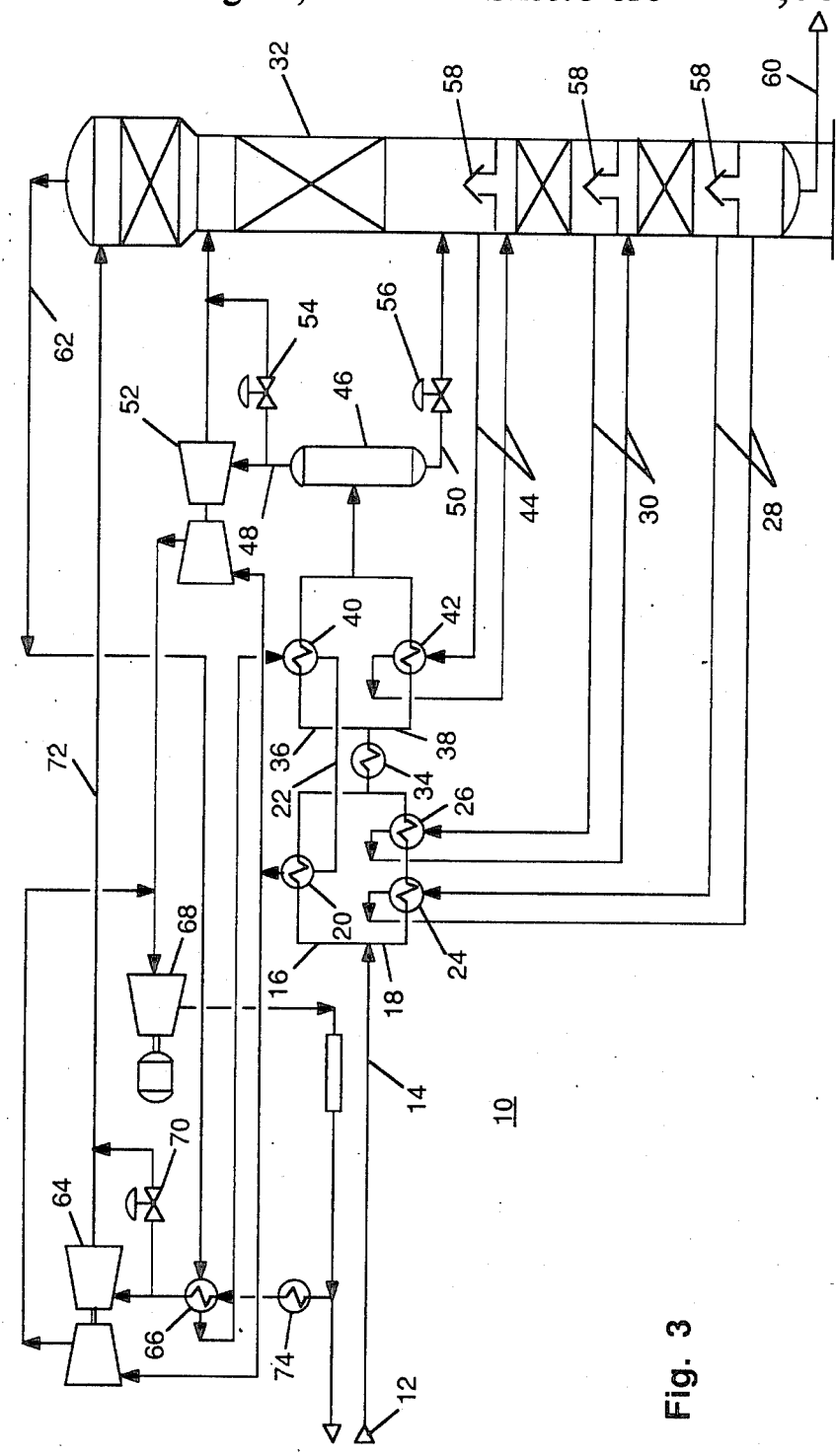
FIG. 3 is a further schematic illustration wherein the reflux line is chilled via multiple heat exchangers.

A further arrangement for gas separator process 10 is shown FIG. 3. In this case, reflux stream 72 is first cooled by another medium such as cooling water or a refrigerant in a separate exchanger 74 before final cooling in reflux exchanger 66.

Depending on the thermodynamic properties of reflux stream 72 and the economics of the project, reflux expander 64 may be used or control valve 70 may be utilized to expand the portion of the residue gas returned to demethanized 32 via reflux stream 72.

The inlet gas cooling arrangement consisting of exchangers 20, 24, 26, 34, 40, and 42 is a typical one. Other exchanger arrangements such as fewer side reboilers or a different refrigerant exchanger location may be utilized.

What is claimed is:

1. A process for separating the constituents of a natural gas stream comprising:
   (a) lowering the temperature of said gas stream;
   (b) supplying said lower temperature gas stream to a high pressure separator, said high pressure separator separating said gas stream into predominantly vapor and predominantly fluid streams;
   (c) lowering the pressure of said predominantly vapor stream;
   (d) supplying said lower pressure vapor stream to an upper region of a demethanizer column;
   (e) lowering the pressure of said predominantly fluid stream;
   (f) supplying said lower pressure fluid stream to said demethanizer column at an elevation below said vapor stream;
   (g) removing cold vapor residue gas from an upper region of said demethanizer column, said vapor residue gas comprising predominantly of methane and other residual light vapors;
   (h) passing said vapor residue gas through at least one heat exchanger to raise the temperature of said vapor residue gas;
   (i) compressing said vapor residue to a higher pressure;
   (j) drawing off a portion of said higher pressure vapor residue;
   (k) lowering the temperature of said drawn off higher pressure vapor residue.
   (l) lowering the pressure of said higher pressure residue to produce a predominantly liquid stream;
   (m) supplying said lower temperature predominantly liquid stream as reflux to the top of said demethanizer column whereby the addition of said reflux alters the chemical equilibrium existing in the top of said demethanizer column thereby enhancing the separation of the inlet stream constituents in said demethanizer column; and,
   (n) removing a demethanized liquid product from a lower region of said demethanizer column.

2. A process as set forth in claim 1 wherein the temperature of said gas stream is lowered by separating said stream into two streams and cooling said streams in gas heat exchangers.

3. A process as set forth in claim 2 wherein said gas heat exchangers use said cold vapor residue gas as a refrigerant and said demethanized liquid product as a refrigerant.

4. A process as set forth in claim 3 wherein the pressure of said predominantly vapor stream is lowered across expansion means.

5. The process as set forth in claim 4 wherein said expansion means comprise a main expander.

6. A process as set forth in claim 4 wherein said expansion means comprise on in-line expansion valve.

7. A process as set forth in claim 4 wherein the pressure of said predominantly fluid stream is lowered across and in-line expansion valve.

8. A process as set forth in claim 7 wherein said cold vapor residue gas is compressed on the compressor side of an expander.

9. A process as set forth in claim 8 wherein the temperature of said drawn off vapor residue gas is lowered in a heat exchanger using cold vapor residue gas a refrigerant.

10. A process as set forth in claim 8 wherein the pressure of said drawn off vapor is lowered across expansion means.

11. A process as set forth in claim 10 where said expansion means comprise a reflux expander.

12. A process as set forth in claim 10 wherein said expansion means comprise an in-line flash valve.

13. A process as set forth in claim 10 wherein the temperature of said gas stream is lowered in a chiller.

14. A process as set forth in claim 13 wherein said demethanizer tower in a natural gas extraction plant is a distillation tower having a reboiler system and a flux system.

* * * * *